United States Patent [19]

Engel et al.

[11] Patent Number: 4,647,704

[45] Date of Patent: Mar. 3, 1987

[54] HYDROCRACKING PROCESS FOR LIQUEFACTION OF LIGNIN

[75] Inventors: Dusan J. Engel, Des Plaines; Karl Z. Steigleder, Glen Ellyn, both of Ill.

[73] Assignee: UOP Inc., Des Plaines, Ill.

[21] Appl. No.: 856,313

[22] Filed: Apr. 28, 1986

[51] Int. Cl.$^4$ .................. C07C 37/52; C07C 39/00
[52] U.S. Cl. ................................... 568/716; 568/761
[58] Field of Search ............................... 568/716, 761

[56] References Cited

U.S. PATENT DOCUMENTS

| | | | |
|---|---|---|---|
| 2,870,133 | 1/1959 | Giesen | 568/761 |
| 3,105,095 | 7/1963 | Oshima et al. | 568/761 |
| 3,223,698 | 12/1965 | Oshima et al. | 568/761 |
| 3,987,114 | 10/1976 | Albright et al. | 568/761 |

FOREIGN PATENT DOCUMENTS

| | | | |
|---|---|---|---|
| 700210 | of 0000 | Canada | 568/761 |
| 851708 | 9/1970 | Canada | 568/761 |
| 26668 | 12/1963 | Japan | 568/761 |
| 151900 | 12/1975 | Japan | 568/761 |

OTHER PUBLICATIONS

Hastbacka and Bredenberg, *Paperi ja Puu*, 55 (3), 1973.
Gendler et al., Wood Agric. Residues: Res. Use Feed, Fuels, Chem., J. Soltes, Ed. (Academic Press, 1983), pp. 391–400.
R. W. Coughlin et al., *Bioconvers. Syst.*, 1984, D. L. Wise, Ed. (CRC), 49–50.
F. P. Petrocelli and M. T. Klein, Ann. Meeting of American Insti. of Chem. Eng., Nov. 1984, San Francisco, CA.

*Primary Examiner*—Werren B. Lone
*Attorney, Agent, or Firm*—Thomas K. McBride; John F. Spears, Jr.; Eugene I. Snyder

[57] ABSTRACT

Hydrocracking of lignin in the presence of a supported tungsten-nickel catalyst affords phenolic compounds in higher yield and with greater selectivity then previously obtainable. Mildly acidic supports, such as alumina, alumina-silica, aluminum phosphate, and silica-aluminum phosphate, have been found to be particularly effective. When the hydrocracking is done in the presence of water, a lower aliphatic alcohol, or a Lewis acid such as ferrous chloride, increased yields of both cresols and $C_6$–$C_8$ and $C_6$–$C_9$ phenolics are obtained.

13 Claims, No Drawings

HYDROCRACKING PROCESS FOR LIQUEFACTION OF LIGNIN

BACKGROUND OF THE INVENTION

Lignocellulosic materials represent a vast amount of renewable resources available in virtually every part of the world. The use of lignocellulosics as a raw material for chemicals continues to be limited by the nature of current delignification processes (i.e., separation of lignin from cellulosic and hemicellulosic components) and by the difficulty of converting the lignin obtained to articles of commerce. This application is directed toward the latter. More particularly, this application is directed to the hydrogenolysis of a species of lignin to afford phenols, especially cresols.

Catalytic hydrogenolysis of lignin was known for some time to effect liquefaction, but its utility was severely curtailed by its tendency to afford a product of little commercial value. With the advent of the so-called Noguchi process (Canadian Pat. No. 700,210) it was claimed that a mixture of $C_6$–$C_9$ monophenols would be obtained upon hydrogenolysis in yields as high as about 40%. The patentee used a catalyst of iron(II) sulfide with a co-catalyst of at least one sulfide of copper, silver, tin, cobalt, chromium, nickel, zinc, or molybdenum, and conducted the reaction in a solvent such as lignin tars and phenols at 250°–450° C. and an initial hydrogen pressure of 150–450 atmospheres. The process was extensively evaluated (David W. Goheen, Lignin Structure and Reactions, American Chemical Society, Advances in Chemistry Series, No. 59) in a multitude of its variants, and although the high yields of monophenols as claimed by the patentee never could be reproduced the investigators concluded that the process remained the best one for lignin liquefaction to that date. However, another conclusion was that the process, even though the best one available, was economically unattractive because of the kind of lignin used, the relatively low economic value of the monophenol product mixture, and the loss of phenol itself when used as a solvent.

More recently research directed toward obtaining useful monomeric products, especially phenolics, from lignin has turned toward the hydrocracking of lignin. Hydrocracking catalysts, used endemically in the petroleum industry, are bifunctional supported metal catalysts having both cracking and hydrogenation activity. Cracking activity generally arises from the support itself, most often through acidic sites, as well as from at least one supported metal, whereas hydrogenation activity usually arises from a supported metal generally recognized as a hydrogenation catalyst. In one of the few published reports directed toward hydrocracking of lignin Hastbacka and Bredenberg, *Paperi ja Puu*, 55 (3), 1973, used a nickel-molybdenum combination on a silica-alumina support, with most of their efforts directed toward hydrocracking of model compounds rather than lignin itself. Gendler et al., *Wood Agric. Residues: Res. Use Feed, Fuels, Chem., Proc. Conf. Feed, Fuels, Chem., Wood Agric. Residues*, 1982, J. Soltes, Ed. (Academic Press, 1983), 391–400, have described lignin hydrocracking using an unspecified catalyst in an ebullated bed. Compare R. W. Coughlin et al., *Bioconvers. Syst.*, 1984, D. L. Wise Ed., (CRC), 49–50. The use of $CoO$—$MoO_3$ on gamma-alumina in hydrocracking various compounds used as models for lignin was recently described by F. P. Petrocelli and M. T. Klein, Ann. Meeting of American Institute of Chemical Engineers, November, 1984, San Francisco, CA.

We have found a hydrocracking process using a supported nickel-tungsten catalyst which affords phenolics in high yield with little consumption of the phenol used as the pasting oil (lignin solvent). More particularly, when the hydrocracking of lignin is effected with the aforementioned catalyst in the presence of a lower aliphatic alcohol, especially in the presence of both a lower aliphatic alcohol and a Lewis acid which also is a Friedel-Crafts catalyst, and even more preferably in the presence of up to about 25% water as well, good yields of phenols, and especially cresols, can be obtained with high liquefaction of lignin.

SUMMARY OF THE INVENTION

The purpose of this invention is to liquefy and depolymerize lignin to phenolics in good yield. An embodiment comprises reacting a solution of lignin with a catalyst of nickel and tungsten supported on alumina, aluminum phosphate, silica, and combinations thereof in a hydrogen atomsphere at a temperature between about 300° and 450° C. In a more specific embodiment the support is silica-alumina. In another embodiment the reaction medium contains a lower aliphatic alcohol. In yet another embodiment the reaction is performed in the presence of a Lewis acid which also is a Friedel-Crafts catalyst. Other embodiments will be apparent from the description which follows.

DESCRIPTION OF THE INVENTION

The invention herein is a method of converting lignin to nomomeric hydroxyaromatic compounds, i.e., phenols. It arises from our observation that hydrocracking lignin using a hydrocracking catalyst of tungsten and nickel on a mildly acidic support affords phenols, especially cresols, in higher yield than that attending use of other hydrocracking catalysts. The invention arises from the further discovery that when hydrocracking is performed in the presence of a lower aliphatic alcohol, especially methanol, the yield of phenols—cresols where methanol is used—is substantially enhanced. A further discovery leading to the invention herein is that when the reaction is performed in the presence of both a Lewis acid which is a Friedel-Crafts catalyst and a lower aliphatic alcohol the yield of phenols is increased still further. A final observation leading to out invention is that the presence of water, in amounts as great as 25%, leads to higher yields of phenols.

The lignin which is used in our process most usually is lignin arising from the Kraft process, but is not limited thereto. Only non-basic lignin may be used, because as pointed out below cracking activity is associated with the acidic sites of the catalyst support, and the presence of base is deleterious in the practice of our invention. Consequently the use of such materials as lignosulfonate salts is to be avoided.

The lignin is first dissolved in a suitable solvent with hydroxyaromatics (phenols) the solvents of choice, and phenol itself, $C_6H_5OH$, being the solvent of choice. Although other solvents such as lignin tars and high boiling hydrocarbons also may be used, we have observed that the extent of liquefaction is greater when phenols are the solvent than when the other mentioned materials are used. This is not to say that phenols are necessarily the ideal solvent; rather it means that in our limited experience phenols as a class afford better product yield than the other materials we have tested. It needs to be emphasized that any solvent which is unreactive under the conditions of our process and which leads to greater than about 90% lignin liquefaction may be used in the practice of our invention. A ratio of solvent to lignin from about 1.5 to about 2.5 appears adequate but is in no way critical to the success of our invention.

The solution of lignin is then reacted with hydrogen at elevated pressure and temperature in the presence of a hydrocracking catalyst. Such a catalyst is a composite of one or more metals on a support. A hydrocracking catalyst is characterized as being a bifunctional catalyst with one component having good cracking activity and the other component having good hydrogenation/hydrogenolytic activity. In the hydrocracking catalysts of interest in this invention the tungsten component and the support itself generally exhibit good cracking activity toward lignin, i.e., they depolymerize lignin and afford a mixture of shorter chain materials. The other component of the catalyst of this invention is a metal, such as nickel, which exhibits both good hydrogenation and hydrogenolytic activity.

It has been found that the supports of choice in the practice of this invention are mildly acidic supports. This means that the support does not contain strong acids; although alumina itself is acceptable, fluorided alumina is to be avoided in the practice of this invention. Similarly, the support should not contain alkali metals; alumina doped with sodium or lithium is not a recommended support. Among the supports which may be used in the practice of this invention are alumina, silica, aluminum phosphate, zirconia, titania, lanthanum phosphate, and combinations thereof. Among the preferred supports are alumina, aluminum phosphate, silica-alumina, and silica-aluminum phosphate, with the latter two being somewhat more favored.

The catalysts of this invention are a composite of tungsten on one of the aforementioned supports. Tungsten generally is initially present as the oxide, although it is reduced under reaction conditions to the zerovalent metal. Tungsten also may be sulfided under the reaction conditions, and in fact supported tungsten sulfide alone is a usable catalyst although it is somewhat less desirable than the nonsulfided tungsten counterpart. Tungsten shows activity for both cracking and hydrogenolysis of lignin. Therefore, tungsten may be used alone, especially as its sulfide, although even better results may be obtained with a second metal component. In either event the catalyst generally contains from about 2% to about 20% by weight of tungsten based on the finished catalyst.

Of the second metal components of our hydrocracking catalyst nickel has been found to be most useful. However, nickel can be replaced by palladium or cobalt, although not necessarily with equivalent results. Such metals often initially are present as the oxide, or the oxide of such metals is formed during calcination of the composite, but in any event the metal is reduced to the zerovalent state under the reaction conditions. When a second metal is present in the catalyst the weight ratio of tungsten to the second metal is in the range from about 1:1 to about 100:1. In the case of nickel a tungsten-to-nickel ratio from about 5:1 to about 20:1 is preferred.

It has been found that the presence in water in an amount up to about 25% by weight relative to lignin increases the yield of $C_6$–$C_8$ and $C_6$–$C_9$ phenolics, especially of phenol itself. An amount of water not greater than about 10% is generally desired since it has been observed under some reaction conditions that the yield of cresol may be lowered by the presence of additional water.

It also has been found beneficial that the reaction mixture contain a lower saturated aliphatic alcohol, which is to say an alcohol containing from 1 to about 4 carbon atoms. Such an alcohol includes methanol, ethanol, n-propanol, i-propyl alcohol, n-butanol, i-butyl alcohol, s-butyl alcohol, and t-butyl alcohol, with methanol being the alcohol of choice. Where, for example, methanol is added this leads to increased cresol formation as well as increased yields of both total $C_6$–$C_8$ and $C_6$–$C_9$ phenols. Such alcohols may be added in an amount up to about 25%, although usually they are added in an amount from about 5% to 20%, even more usually between about 7% and about 15%, the percentages being by weight based on lignin.

We have observed that the presence of Lewis acids which also are Friedel-Crafts catalysts exert a beneficial affect upon the course of the reaction. So, for example, salts of iron, antimony, tin, zinc and aluminum are particularly desirable. Although the chlorides and bromides are most usually used, other salts such as the fluorides and phosphates may be employed, but not necessarily with equivalent results. Where present in the reaction mixture, such salts are used in an amount from about 0.5 to about 5 weight percent based on the lignin present. The Lewis acids also may be deposited on the support directly, although not necessarily with equivalent results, and since such materials often are calcined after impregnation they may be present as the oxide. Under the reaction conditions such materials usually are reduced to the metal, at least where iron, antimony, and tin are employed.

Hydrocracking of lignin is performed at a temperature between about 300° and about 450° C. At higher temperatures excessive amounts of insoluble and intractable materials may be formed, whereas at lower temperatures the rate of reaction may be too slow to be practical. It has been found that a temperature range between about 375° and about 425° C. is most desirable. Hydrocracking of lignin is performed in an atmosphere of hydrogen where the initial hydrogen pressure is between about 500 psig (3450 kPa) and about 3500 psig (24,150 kPa).

The process which is our invention may be carried out either in a batch mode or in a continuous fashion. Where performed batch-wise, a solution of an acidic lignin in preferably a phenolic solvent is mixed with a hydrocracking catalyst, as described within, in an amount sufficient to afford between about 0.5 and about 5.0 weight percent tungsten based on the lignin present. The reaction mixture also may contain water in an amount up to about 25%, more desirably up to about 10% by weight based on lignin, and/or a lower aliphatic alcohol, preferably methanol, in an amount up to about 15 weight percent based on lignin, and a Lewis acid which is a Friedel-Crafts catalyst, for example, ferrous chloride, in an amount up to about 5 weight percent based on lignin. The reaction mixture may then be pressured with hydrogen in an amount sufficient to afford between about 500 and about 3500 psig (3450 to 24,150 kPa), and the reaction mixture then heated to a temperature between about 300° to about 450° C. Mixing is necessary to afford good contact among the solid, liquid, and gaseous phases, and reaction is continued for a time sufficient to largely liquefy the lignin and to optimize the yields of the desired phenolics. The reaction time will depend upon such variables as the source of lignin, reaction temperature, hydrogen pressure, the amount and nature of the hydrocracking catalyst, and so forth, but typically will be in the range from about 0.3 hours to about 3 hours.

Hydrocracking of lignin according to our invention also may be carried in a continuous fashion. Where a fixed bed is used plugging may be a problem because of formation of hard, insoluble materials during the hydrocracking of lignin. Therefore, a fluidized or ebullated bed may be better procedure to use, but in any event the skilled worker will be able to optimize conditions in a continuous process using well known techniques which will not be further elaborated upon.

The examples which follow are merely illustrative and are intended only to represent various aspects of our invention. Accordingly, our invention is not to be limited thereby in any manner.

EXAMPLE 1

To test various materials as lignin solvents a mixture of 20 g lignin (Indulin AT from Westvaco Corp.) and 50 g solvent was heated in a 300 cc stainless steel stirred autoclave at the indicated temperature for one hour in a hydrogen atmosphere whose initial pressure was 100 atmospheres ($1.01 \times 10^4$ kPa). The cooled reaction mixture was filtered, and the liquid was examined by gas-liquid partition chromatography, the components being reported as weight percent of the total eluant. The column headed "lites" refers to components eluted before phenol or anisole using a glass capillary column wall-coated with a bonded methyl silicone phase. The percent liquefaction is at least $100[(1-\text{residue}/\text{lignin charge})]$.

TABLE 1

Thermal Dissolution of Lignin in Solvents - No Catalyst

| Solvent | T° C. | Lites | Phenol | Unknown | Cresols o- | Cresols m + p | Xylenols | $C_8{}^+$ | Phenol formed, g | Percent liquefaction |
|---|---|---|---|---|---|---|---|---|---|---|
| Phenol | 300 | 2.6 | 85.0 | — | 0.4 | 0.2 | 3.1 | 8.6 | 5.1 | 97.4 |
| Phenol | 400 | 3.0 | 79.2 | 0.2 | 5.2 | 2.8 | 3.3 | 6.3 | (−1.1) | 76.5 |
| Tetralin | 300 | Very littles phenolics. Mostly unchanged tetralin. | | | | | | | | 78.5 |
| Tetralin | 400 | 0.9 | 0.4 (68.0) tetralin | 23.4 naphthalene | 0.1 | 1.0 | 1.5 | 4.2 | +0.2 | 96.0 |
| Cat. Cracker Bottoms | 300 | 0.3 | tr. | — | 0.1 | 0.7 | 0.2 | 98.7 | 0 | 85.0 |

The results of Table 1 clearly show the efficacy of phenol as a solvent for lignin, especially at 300° C. On this basis several phenolic materials were compared as solvents in the presence of a hydrocracking catalyst. In these experiments, summarized in Table 2, 5 g of a catalyst containing 0.6% Ni and 6% W on a 50/50 silica-alumina base was used in a mixture containing 50 g of the phenol and 20 g lignin at 400° C., 100 atmospheres ($1.01 \times 10^4$ kPa) initial pressure hydrogen for a reaction time of 1 hour. As the results show, phenol and cresol are of similar efficacy in liquefying lignin while o-xylenol is slightly inferior in both liquefaction and net solvent weight change.

TABLE 2

Lignin Depolymerization - Effect of Phenolic Solvents

| Solvent | Lites | Pehnol | Unknown | Cresols o- | Cresols m + p | Xylenols | $C_g$ | $C_{10}$ | Solvent weight change, g | Lignin Liquefaction % |
|---|---|---|---|---|---|---|---|---|---|---|
| Phenol | 1.6 | 80.0 | 0.1 | 5.1 | 3.6 | 3.0 | 6.6 | | +0.8 | 92.4 |
| o-Cresol | 1.5 | 5.5 | 1.9 | 71.7 | | 10.6 | 2.6 | 6.2 | −0.7 | 93.0 |
| 2,6-Xylenol | 1.2 | 1.3 | 0.3 | 11.0 | | 73.6 | 6.3 | 6.2 | −6.1 | 89.6 |

EXAMPLE 2

The cracking characteristics of various supports toward lignin were determined by charging a mixture of 50 g phenol, 20 g lignin, and 5 g support with hydrogen to a pressure of 100 atmospheres ($1.01 \times 10^4$ kPa) and heating the mixture to 400° C. for 1 hour. When $La_3(PO_4)_2$ was used there was added 10 g water. As Table 3 shows, base activity in lignin liquefaction is $AlPO_4 > SiO_2/AlPO_4 > Al_2O_3 > La_3(PO_4)_2 > ZrO_2 > TiO_2$. Silica-alumina is somewhat more effective than alumina itself. The results in Table 3 tend to indicate that slightly acidic or neutral supports are more suitable than slightly basic ones.

TABLE 3

Lignin Depolymerization - Effect of Catalyst Bases

| Catalyst Bases | Lites | Phenol | Unknown | Cresols o- | Cresols m + p | Xylenols | $C_9+$ | Phenol spent, g | Lignin Liquefaction % |
|---|---|---|---|---|---|---|---|---|---|
| $Al_2O_3$ | 2.1 | 78.4 | 0.1 | 5.8 | 3.2 | 2.7 | 7.7 | −2.9 | 83.3 |
| $ZrO_2Al_2O_3$ 50:50 | 2.4 | 78.2 | 0.2 | 5.9 | 3.4 | 2.7 | 7.2 | −4.1 | 76.5 |
| $TiO_2$ | 2.9 | 79.3 | 0.3 | 5.4 | 2.8 | 2.5 | 4.6 | −7.3 | 73.0 |
| ALPO | 2.8 | 77.6 | 0.4 | 5.8 | 3.6 | 2.8 | 7.0 | −2.0 | 93.0 |
| $SiO_2$ALPO 50:50 | 2.3 | 76.4 | 0.3 | 5.7 | 4.1 | 2.9 | 8.3 | −3.2 | 88.4 |

TABLE 3-continued

| | Lignin Depolymerization - Effect of Catalyst Bases | | | | | | | |
|---|---|---|---|---|---|---|---|---|
| | Product, GC, Wt. % | | | | | | | |
| | | | | Cresols | | | Phenol | Lignin |
| Catalyst Bases | Lites | Phenol | Unknown | o- | m + p | Xylenols | $C_9+$ | spent, g | Liquefaction % |
| $La_3(PO_4)_2$ | 2.9 | 73.0 | 0.3 | 4.7 | 3.0 | 3.8 | 12.3 | −0.9 | 76.0 |

EXAMPLE 3

Representative data showing the effect of several variable on lignin liquefaction are given in Table 4. Unless otherwise stated, the reaction mixture of 50 g phenol, 20 g lignin, and 5 g catalyst containing 0.6% Ni and 6% W (as their oxides) on a silica-alumina support was charged with hydrogen to 100 atmospheres ($1.01 \times 10^4$ kPa) and heated for 1 hour at the indicated temperature. Runs 1–4 show the effect of temperature over a limited range. In run 5 a sulfided catalyst was used, which means the hydrocracking catalyst was contacted with a mixture of 10% hydrogen sulfide—90% water at 775° F. (413° C.) for 3 hours. Runs 6 and 7 demonstrate the effect of water added to the reaction mixture. Runs 8 and 9 show results with recycled catalyst where methanol (15% by weight based on lignin) was added to recycled catalyst. Runs 10, 11 show similar results using a catalyst of 0.6% Ni and 6%W on $AlPO_4$. The effect of added methanol using fresh catalyst is shown in run 12, and the effects of $FeCl_2$ with and without methanol, and of iron impregnated on the catalyst are summarized in runs 14, 13, and 15, respectively.

The following conclusions can be drawn from the data presented above. Comparison of runs 1, 2 with 3, 4 show that although lignin liquefaction and cresol yields are increased at higher temperature the increase comes at the cost of phenol (solvent) consumption. A catalyst with sulfided metals is somewhat inferior to that with nonsulfided metals (run 5 versus 1, 2), but since the sulfur content of a lignin feedstock also will cause sulfidation the data show that the catalyst will not be inactivated by sulfur. Addition of water up to about 25% by weight based on lignin affords improved yield of phenols in the $C_6$–$C_8$ and $C_6$–$C_9$ range (runs 6–7), and methanol affords substantially improved yields of cresols and other phenolics in both recycled (run 9) and fresh catalyst (run 12). Comparison of runs 1 and 8, and runs 10 and 11, shows that catalyst can be readily recycled. The beneficial effects of a Lewis acid and Friedel-Crafts catalyst, $FeCl_2$, are shown in run 13, with such effects being accentuated by the addition of methanol (run 14) and remaining even when the iron is deposited on the catalyst as the oxide (run 15).

TABLE 4

| | | Effect of Variables on Lignin Liquefaction and Depolymerization Using Hydrocracking Catalyst | | | | |
|---|---|---|---|---|---|---|
| | | Phenol formed(+) or spent (−), g | Lignin Liquefaction % | Yield, wt/wt Lignin, % | | |
| Run | T° C. | | | Cresols | Phenols $C_6$–$C_8$ | Phenols $C_6$–$C_9$ |
| 1 | 400 | +0.8 | 92.4 | 27.5 | 41.0 | — |
| 2 | 400 | −0.9 | 94.3 | 28.0 | 37.0 | — |
| $3^a$ | 450 | −3.5 | 98.0 | 30.0 | 40.5 | — |
| 4 | 450 | −7.8 | 100.0 | 30.5 | 46.0 | — |
| 5 | 400 | −1.4 | 96.8 | 20.0 | 28.0 | — |
| $6^b$ | 400 | +2.2 | 92.6 | 27.5 | 47.5 | 52.5 |
| $7^c$ | 400 | +3.2 | 100.0 | 26.5 | 51.0 | 55.6 |
| $8^d$ | 400 | +4.6 | 100.0 | 20.0 | 50.5 | 55.5 |
| $9^{e,f}$ | 400 | −3.6 | 100.0 | 31.1 | 52.0 | 57.6 |
| $10^g$ | 400 | +1.3 | 100.0 | 27.5 | 42.5 | 46.5 |
| $11^{d,f,g}$ | 400 | −0.1 | 100.0 | 17.2 | 45.5 | 49.0 |
| $12^f$ | 400 | −1.3 | 95.5 | 34.0 | 41.5 | 45.5 |
| $13^h$ | 400 | +2.1 | 94.5 | 26.5 | 45.0 | 49.5 |
| $14^{f,h}$ | 400 | −1.9 | 89.5 | 44.5 | 55.5 | 60.0 |
| $15^{f,i}$ | 400 | −0.4 | 94.0 | 37.5 | 48.0 | 53.0 |

$^a$Reaction time was only 0.5 hours.
$^b$Reaction mixture contained 10 weight percent water based on lignin.
$^c$Reaction mixture contained 25 weight percent water based on lignin.
$^d$Recycled catalyst.
$^e$Twice recycled catalyst.
$^f$15 weight percent methanol added based on lignin.
$^g$Catalyst support was $AlPO_4$.
$^h$Contained $FeCl_2 \times 3H_2O$, 3 weight percent based on lignin.
$^i$Catalyst composite contained 3 weight percent iron.

What is claimed is:

1. A method of hydrocracking lignin to produce monomeric hydroxyaromatic compounds comprising reacting a solution of a non-basic lignin with hydrogen at a pressure from about 500 to about 3500 psig and a temperature from about 300° to 450° C. in the presence of a hydrocracking catalyst, said catalyst being a cracking support selected from the group consisting of alumina, silica, silica-alumina, aluminum phosphate, silica-aluminum phosphate, zirconia, titania, lanthanum phosphate, and combinations thereof, and said support containing from about 2% to about 20% by weight of tungsten as zero-valent or sulfided tungsten and a second component selected from the group consisting of zerovalent nickel, palladium, and cobalt, the weight ratio of tungsten to said second component being from about 1:1 to about 100:1, and collecting the reaction product.

2. The method of claim 1 where the support is silica-alumina or silica-aluminum phosphate.

3. The method of claim 1 where the tungsten is present as the sulfide.

4. The method of claim 1 where tungsten is present in its zerovalent state.

5. The method of claim 1 where the second component is nickel.

6. The method of claim 5 where the weight ratio of tungsten to nickel is from about 5:1 to about 20:1.

7. The method of claim 1 where the lignin is that obtained from the Kraft process.

8. The method of claim 1 where the solution is a phenolic solution.

9. The method of claim 1 further characterized in that the reaction is performed in the presence of water in an amount up to about 25% by weight based on lignin.

10. The method of claim 1 further characterized in that the reaction is performed in the presence of a lower saturated aliphatic alcohol in an amount up to about 15% by weight based on lignin.

11. The method of claim 10 where the alcohol is methanol.

12. The method of claim 1 further characterized in that the reaction is performed in the presence of a Lewis acid which is also a Friedel-Crafts catalyst in an amount up to about 10% by weight based on lignin.

13. The method of claim 12 where the catalyst contains iron.

* * * * *